United States Patent [19]

Fiedler et al.

[11] Patent Number: 4,536,344

[45] Date of Patent: Aug. 20, 1985

[54] PROCESS FOR FORMYLATING ARYL HALIDES

[75] Inventors: Paul Fiedler, Cologne; Rudolf Braden, Odenthal, both of Fed. Rep. of Germany

[73] Assignee: Bayer Aktiengesellschaft, Leverkusen, Fed. Rep. of Germany

[21] Appl. No.: 549,339

[22] Filed: Nov. 4, 1983

[30] Foreign Application Priority Data

Nov. 18, 1982 [DE] Fed. Rep. of Germany ....... 3242582

[51] Int. Cl.$^3$ .............................................. C07C 45/49
[52] U.S. Cl. ................................ 260/465 R; 568/428; 568/41; 568/311; 560/51; 549/70; 546/314

[58] Field of Search .......................... 568/428, 41, 311; 260/465 R; 560/51; 549/70; 546/314

[56] References Cited

U.S. PATENT DOCUMENTS 3,960,932  6/1976  Heck .............................. 568/428 X

*Primary Examiner*—Bernard Helfin
*Attorney, Agent, or Firm*—Sprung, Horn, Kramer & Woods

[57] ABSTRACT

Aryl halides are formylated with carbon monoxide and hydrogen in the presence of a noble metal catalyst, tertiary organic nitrogen compounds and phosphanes or phosphites.

10 Claims, No Drawings

PROCESS FOR FORMYLATING ARYL HALIDES

The invention relates to a process for formylating aryl halides with carbon monoxide and hydrogen in the presence of a noble metal catalyst, tertiary organic nitrogen compound and phosphane and/or phosphite as a promoter.

The formylation of aryl bromides and aryl iodides is known (J. Am. Chem. Soc. 96, 7761 (1974)). In these processes the reaction takes between 9 and 72 hours, which corresponds to a space-time yield of 6.5 to 0.7 g/liter per hour, and catalyst consumption is between 5 and 16%, relative to the reaction mixture used.

This known process is therefore not used in industry.

We have found a process for formylating optionally substituted iodo-, bromo- and/or chloro-aryl radicals with carbon monoxide and hydrogen within the pressure range from 20 to 400 bar and within the temperature range from 80° to 250° C. in the presence of a noble metal catalyst and a tertiary organic nitrogen compound, which is characterized in that a phosphane and/or a phosphite is added.

Phosphanes of the formula

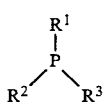
(I)

and phosphites of the formula

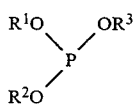
(II)

in which $R^1$, $R^2$ and $R^3$ are identical or different and denote alkyl, cycloalkyl, aryl or aralkyl and the radicals can be optionally substituted by hydroxyl, alkoxy, carbalkoxy, amino or halogen, may be mentioned for use in the process of the invention.

Phosphanes of the formula

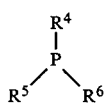
(III)

and phosphites of the formula

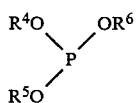
(IV)

in which $R^4$, $R^5$ and $R^6$ are identical or different and denote alkyl having 1 to 20 carbon atoms, cycloalkyl having 5 to 12 carbon atoms, aralkyl radicals having 7 to 12 carbon atoms or aryl radicals having 6 to 18 carbon atoms and the radicals can be optionally substituted by hydroxyl, lower alkoxy, lower carbalkoxy, fluorine, chlorine or amino of the formula

in which $R^7$ and $R^8$ are identical or different and denote lower alkyl or the group

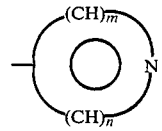

in which the total number of ring atoms is 5 or 6 and m and n represent 0, 1 or 2, may be mentioned as preferred for the process of the invention.

For the purpose of the invention, alkyl can be a straight-chain or branched hydrocarbon radical having 1 to 20, preferably 1 to 12, carbon atoms. The lower alkyl radical having 1 to about 6 carbon atoms is particularly preferred. The following alkyl radicals may be mentioned by way of example: methyl, ethyl, propyl, isopropyl, butyl, isobutyl, pentyl, isopentyl, hexyl and isohexyl.

For the purposes of the invention, cycloalkyl can be a cyclic hydrocarbon radical having 5 to 12, preferably 5 to 7, carbon atoms. The cyclopentyl, the cyclohexyl and the cycloheptyl radicals may be mentioned as particularly preferred.

For the purposes of the invention, aralkyl radicals can be aryl-substituted alkyl radicals which consist of a straight-chain or branched hydrocarbon radical having 1 to 6 carbon atoms in the aliphatic moiety and of a radical of the benzene series, preferably phenyl, in the aromatic moiety. The benzyl radical may be mentioned as an example of an aralkyl radical.

For the purposes of the invention, aryl can be an aromatic hydrocarbon radical from the benzene series having 6 to 18, preferably 6 to 12, carbon atoms. The following aryl radicals may be mentioned by way of example: phenyl, biphenyl, naphthyl and antracyl.

The lower alkoxy and lower carbalkoxy radicals consist in the aliphatic moiety of a straight-chain or branched hydrocarbon radical having 1 to about 6 carbon atoms. The following lower alkoxy radicals may be mentioned by way of example: methoxy, ethoxy, propoxy, isopropoxy, butoxy, isobutoxy, pentoxy, isopentoxy, hexoxy and isohexoxy.

The following lower carbalkoxy radicals may be mentioned by way of example: carbomethoxy, carbethoxy, carbisopropoxy and carbopropoxy.

For the purposes of the invention, halogen can be fluorine or chlorine, preferably fluorine.

The phosphanes for the process of the invention are known per se (Houben-Weyl, Meth. der Org. Chem. [Methods of Organic Chemistry], Volume XII/1).

For example, they can be prepared by reacting $PCl_3$ with appropriate Grignard compounds.

Phosphites for the process of the invention are known per se (Houben-Weyl, Meth. d. Org. Chemie [Methods of Organic Chemistry] Volume XII/2).

For example, they can prepared by reacting alcohols with phosphorus trichloride in the presence of an acid-binding agent such as triethylamine.

The following phosphanes and phosphites may be mentioned by way of example: triphenylphosphane, triphenyl phosphite, diethylphenylphosphane, diethylphenyl phosphite, tritolylphosphane, tritolyl phosphite, trinaphthylphosphane, trinaphthyl phosphite, diphenylmethylphosphane, diphenylmethyl phosphite, diphenylbutylphosphane, diphenylbutyl phosphite, tris-(p-carbomethoxyphenyl)-phosphane, tris-(p-carbomethoxyphenyl) phosphite, tris-(p-cyanophenyl)-phosphane, tris-(p-cyanophenyl) phosphite, triethyl phosphite, tributylphosphane, tributyl phosphite, P[CH$_2$CH$_2$CH$_2$N(CH$_3$)$_2$]$_3$, P[OCH$_2$CH$_2$CH$_2$N(CH$_3$)$_2$]$_3$, P[CH$_2$CH$_2$CH$_2$N(C$_2$H$_5$)$_2$]$_3$, P[OCH$_2$CH$_2$CH$_2$N(C$_2$H$_5$)$_2$]$_3$, P(CH$_2$CH$_2$CH$_2$—N-H—iso-C$_4$H$_9$)$_3$, P(OCH$_2$CH$_2$CH$_2$—NH—iso-C$_4$H$_9$)$_3$, P[CH$_2$CH$_2$CH$_2$N(iso-C$_4$H$_9$)$_2$]$_3$, P[OCH$_2$CH$_2$CH$_2$N(iso-C$_4$H$_9$)$_2$]$_3$, (n—C$_4$H$_9$)$_2$PCH$_2$CH$_2$N(C$_2$H$_5$)$_2$, P[CH$_2$N(C$_2$H$_5$)$_2$]$_3$, P[OCH$_2$N(C$_2$H$_5$)$_2$]$_3$, P[C$_6$H$_4$N(CH$_3$)$_2$]$_3$, P[OC$_6$H$_4$N(CH$_3$)$_2$]$_3$, P[CH$_2$CH$_2$C$_6$H$_4$N(C$_2$H$_5$)$_2$]$_3$, P[OCH$_2$CH$_2$C$_6$H$_4$N(C$_2$H$_5$)$_2$]$_3$,

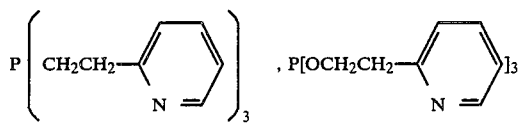

P[CH$_2$CH$_2$CH$_2$N(tert.C$_4$H$_9$)$_2$]$_3$, P[OCH$_2$CH$_2$CH$_2$N(tert.C$_4$H$_9$)$_2$]$_3$, P[CH$_2$CH$_2$CH$_2$N(iso-C$_3$H$_7$)$_2$]$_3$ und P[OCH$_2$CH$_2$CH$_2$N(iso-C$_3$H$_7$)$_2$]$_3$.

Triarylphosphanes, such as triphenylphosphane and tritolylphosphane, are particularly preferred phosphanes.

In the process of the invention the phosphanes and phosphites essentially have a promoting action.

The phosphanes and phosphites are used in an amount which corresponds to 2 to 10$^5$ times the molar amount of catalyst. More particularly, the amount of phosphanes and phosphites used is 10 to 1,000 times the molar amount of catalyst.

The noble metal catalyst used in the process of the invention is a group VIII noble metal of Mendeleyev's periodic table of the elements or one of its compounds. The following noble metals may be mentioned by way of example: rhodium, palladium, platinum and iridium, preferably palladium.

Complexes of the noble metals with the said phosphanes or phosphites may be mentioned as compounds of the noble metals. It is advantageous to use noble metal complexes of those phosphanes or phosphites which are also used as promoters. However, it is of course also possible to use other phosphanes and phosphites as ligands of the noble metals.

The noble metal catalyst is used in an amount of 10$^{-5}$ to 2×10$^{-2}$ mol, preferably 10$^{-4}$ to 10$^{-2}$ mols, relative to the starting compound.

Tertiary organic nitrogen compounds for the process of the invention can be compounds of the formula $$\underset{R^{10}}{\overset{R^9}{\underset{|}{N}}}R^{11} \qquad (V)$$

in which $R^9$, $R^{10}$ and $R^{11}$ are identical or different and denote alkyl having 1 to 20 C atoms or cycloalkyl having 5 to 12 C atoms.

The use of tertiary organic nitrogen compounds for formylation reactions is known per se (J. Am. Chem. Soc. 96, 7761 (1974)).

Those tertiary organic nitrogen compounds are preferred which have the formula

in which $R^{12}$, $R^{13}$ and $R^{14}$ are identical or different and denote alkyl having 1 to 6 C atoms or cycloalkyl having 5 to 8 C atoms.

The following tertiary organic nitrogen compounds may be mentioned as examples: triethylamine, tributylamine, and dicyclohexylmethylamine.

In the process of invention at least stoichiometric amounts of the tertiary organic nitrogen compounds are used. It is preferred to use the tertiary organic compound in a ratio of 1:1 to 5:1, relative to the starting compound.

The process of invention is generally carried out within the temperature range from 80° to 250° C., preferably within the temperature range from 100° to 190° C.

The process of the invention is generally carried out within the pressure range from 20 to 400 bar, preferably within the pressure range from 70 to 300 bar.

In the process of the invention, carbon monoxide and hydrogen are generally used in at least a stoichiometric ratio, but preferably in excess, for example up to 1,000 mol %. The mixture of carbon monoxide and hydrogen generally contains carbon monoxide and hydrogen in a volume ratio of 1:4 to 4:1, particularly preferably in a ratio of 2:1 to 1:2.

The tertiary organic nitrogen compound is generally used in a stoichiometric amount, relative to the aryl halide.

The process of the invention is generally carried out in a liquid phase. The liquid reaction medium can either be a mixture of liquids present anyhow (that is to say, a mixture of starting compounds) or can, if desired, also consist of added solvent which is inert under the reaction conditions.

If the process of the invention is carried out in the presence of a solvent, the solvent used is an organic solvent which does not change under the reaction conditions. Examples which may be mentioned of such solvents are alkyl- and alkoxy-substituted benzenes, such as toluene, xylenes and anisole, high-boiling esters, such as dimethyl adipate, esters and ethers of polyols, such as tetraethylene glycol dimethyl ether, cyclic ethers, such as tetrahydrofuran and dioxane, and hydrocarbons, such as cyclohexane and heptane. The solvents preferably used are cyclohexane and toluene.

The invention prescribes that the solvent is used in a ratio of 20:1 to 1:10, relative to the starting compound. A ratio of 5:1 to 1:3 is preferred.

The process of the invention can formylate optionally substituted iodo-, bromo- and/or chloro-aryl compounds.

Aryl halides of the invention are iodo-, bromo- and/or chloro-aryl compounds of the formula $$X_o\!\!-\!\!\underset{}{\underset{}{\bigcirc}}\!\!-\!\!Y_r \qquad (VII)$$

in which

X denotes chlorine, bromine or iodine, o represents one of the numbers 1, 2 or 3, where in the case that o denotes 2 or 3, X can be identical or different, r represents one of the numbers 1, 2, 3, 4 or 5 and Y can be identical or different if r represents one of the numbers 2, 3, 4 or 5, and denotes hydrogen, fluorine, alkyl, aryl or one of the groups $$-OR, \quad -\overset{O}{\underset{\|}{C}}-OR, \quad -O-\overset{O}{\underset{\|}{C}}-R, \quad -OCF_3, \quad -OCCl_3, \quad -SR,$$

$$-CClF_2, \quad -\overset{O}{\underset{\|}{C}}-CClF_2, \quad -CN$$

wherein

R represents alkyl or aryl, and where in the case that two Ys are adjacent, they can be bonded to form a ring.

The optionally substituted iodo-, bromo- and/or chloro-aryl compounds are known per se (Houben-Weyl, Meth. d. Org. Chemie [Methods of Organic Chemistry], Volume V/4), and can be prepared by, for example, reacting the aromatic compound with the corresponding elemental halogen (iodine, bromine or chlorine).

Optionally substituted iodo-, bromo- and/or chloro-aryl aromatics preferred for the process of the invention have the formula $$X_o\!\!-\!\!\underset{}{\underset{}{\bigcirc}}\!\!-\!\!Y'_r \qquad (VIII)$$

in which X, o and r have the abovementioned meaning and Y', if r represents one of the numbers 2, 3, 4 or 5, can be identical or different and denote hydrogen, fluorine, alkyl having 1 to 20 carbon atoms, phenyl or one of the groups —OR', —OCF$_3$, —OCCl$_3$, —SR', —CClF$_2$ or —CN, wherein R' represents alkyl having 1 to 20 carbon atoms or phenyl, and wherein if two Y's are adjacent they can be bonded to form a ring.

Compounds of the formula $$Br\!\!-\!\!\underset{}{\underset{}{\bigcirc}}\!\!-\!\!Y'_r \qquad (IX)$$

in which Y' and r have the abovementioned meaning, are particularly preferably used.

The following optionally substituted iodo-, bromo- and/or chloro-aryl aromatics may be mentioned by way of example: bromobenzene, o-, m- and p-bromotoluene, 2,3-dimethyLbromobenzene, 2,4-dimethylbromobenzene, 2,5-dimethylbromobenzene, 2,6-dimethylbromobenzene, 3,4-dimethylbromobenzene, 3,5-dimethylbromobenzene, bromomesitylene, o-, m- and p-chlorobromobenzene, o-, m- and p-fluorobromobenzene, 2-chloro-3-fluorobromobenzene, 2-chloro-4-fluorobromobenzene, 2-chloro-5-fluorobromobenzene, 2-chloro-6-fluorobromobenzene, 3-chloro-2-fluorobromobenzene, 3-chloro-4-fluorobromobenzene, 3-chloro-5-fluorobromobenzene, 3-chloro-6-fluorobromobenzene, 4-chloro-2-fluorobromobenzene, 4-chloro-3-fluororomobenzene, o-, m- and p-chloroiodobenzene, 2,3-dichloroiodobenzene, 2,4-dichloroiodobenzene, 2,5-dichloroiodobenzene, 2,6-dichloroiodobenzene, 3,4-dichloroiodobenzene, 3,5-dichloroiodobenzene, 2,3,4-trichloroiodobenzene, 2,3,5-trichloroiodobenzene, 2,3,6-trichloroiodobenzene, 2,4,5-trichloroiodobenzene, 2,4,6-trichloroiodobenzene, 3,4,5-trichloroiodobenzene, 2,3,4,5-tetrachloroiodobenzene, 2,3,4,6-tetrachloroiodobenzene, 2,3,5,6-tetrachloroiodobenzene, pentachloroiodobenzene, 2,3-dichlorobromobenzene, 2,4-dichlorobromobenzene, 2,5-dichlorobromobenzene, 2,6-dichlorobromobenzene, 3,4-dichlorobromobenzene, 3,5-dichlorobromobenzene, 2,3,4-trichlorobromobenzene, 2,3,5-trichlorobromobenzene, 2,3,6-trichlorobromobenzene, 2,4,5-trichlorobromobenzene, 2,4,6-trichlorobromobenzene, 3,4,5-trichlorobromobenzene, 2,3,4,5-tetrachlorobromobenzene, 2,3,5,6-trichlorobromobenzene, 2,3,4,6-tetrachlorobromobenzene, pentachlorobromobenzene, o-, m- and p-fluoroiodobenzene, 2,3-difluoroiodobenzene, 2,4-difluoroiodobenzene, 2,5-dichloroiodobenzene, 2,6-difluoroiodobenzene, 3,4-difluoroiodobenzene, 3,5-difluoroiodobenzene, 2,3,4-trifluoroiodobenzene, 2,3,5-trifluoroiodobenzene, 2,3,6-trifluoroiodobenzene, 2,4,5-trifluoroiodobenzene, 2,4,6-trifluoroiodobenzene, 3,4,5-trifluoroiodobenzene, 2,3,4,5-tetrafluoroiodobenzene, 2,3,5,6-tetrafluoroiodobenzene, 2,3,4,6-tetrafluoroiodobenzene, pentafluorobromobenzene, 2,3-difluorobromobenzene, 2,4-difluorobromobenzene, 2,5-difluorobromobenzene, 2,6-difluorobromobenzene, 3,4-difluorobromobenzene, 3,5-difluorobromobenzene, 2,3,4-trifluorobromobenzene, 2,3,5-trifluorobromobenzene, 2,3,6-trifluorobromobenzene, 2,4,5-trifluorobromobenzene, 2,4,6-trifluorobromobenzene, 2,3,4,5-tetrafluorobromobenzene, 2,3,4,6-tetrafluorobromobenzene, 2,3,5,6-tetrafluorobromobenzene, pentafluorobromobenzene, o-, m- and p-trifluoromethylbromobenzene, o-, m- and p-trifluoroiodobenzene, o-, m- and p-trifluoroiodobenzene, o-, m- and p-trifluoromethoxybromobenzene, o-, m- and p-trifluoromethoxyiodobenzene, o-, m- and p-bromophenol ether, o-, m- and p-bromobenzoic acid ester, o-, m- and p-bromophenyl ester, o-, m- and p-difluorochloromethylbromobenzene, o-, m- and p-difluoromethoxybromobenzene, o-, m- and p-bromobenzonitrile, 1-bromonaphthalene, 2-bromonaphthalene, 2-bromothiophene, 3-bromothiophene, 2-bromopyridine, 3-bromopyridine, 4-bromopyridine, 2-bromo-3-methylpyridine, 2-bromo-4-methylpyridine, 2-bromo-5-methylpyridine, 2-bromo-6-methylpyridine, 3-bromo-2-methylpyridine, 3-bromo-4-methylpyridine, 3-bromo-5-methylpyridine, 3-bromo-6-methylpyridine, 4-bromo-2-methylpyridine, 4-bromo-3-methylpyridine, 2-chloro-3-trifluoromethylbromobenzene, 2-chloro-4-trifluoromethylbromobenzene, 2-chloro-5-trifluoromethylbromobenzene, 2-chloro-6-trifluoromethylbromobenzene, 3-chloro-2-trifluoromethylbromobenzene, 3-chloro-4-trifluoromethylbromobenzene, 3-chloro-5-trifluoromethylbromobenzene, 3-chloro-6-trifluoromethylbromobenzene, 4-chloro-2-trifluoromethylbromobenzene, 4-chloro-3-trifluoromethylbromobenzene, 2-chloro-3-trifluoromethoxybromobenzene, 2-chloro-4-trifluoromethoxybromobenzene, 2-chloro-5-trifluoromethoxybromobenzene, 2-chloro-6-trifluoromethoxybromobenzene, 3-chloro-2-trifluoromethoxybromobenzene, 3-chloro-4-trifluoromethoxybromobenzene, 3-chloro-5-trifluoromethoxybromobenzene, 3-chloro-6-trifluoromethoxybromobenzene, 4-chloro-2-trifluoromethoxybromobenzene, 4-chloro-3-trifluoromethoxybromobenzene, 2-trichloromethyl-4-trifluoromethylbromobenzene, 3-trichloromethyl-5-trifluoromethylbromobenzene, 4-trichloromethyl-6-trifluoromethylbromobenzene, 2-trichloromethyl-6-trifluoromethylbromobenzene, 4,4'-bis-bromophenoxymethane, 4,4'-bis-bromophenoxyethane and 4,4'-bis-bromophenoxypropane.

The process of the invention can be illustrated by, for example, the following equation:

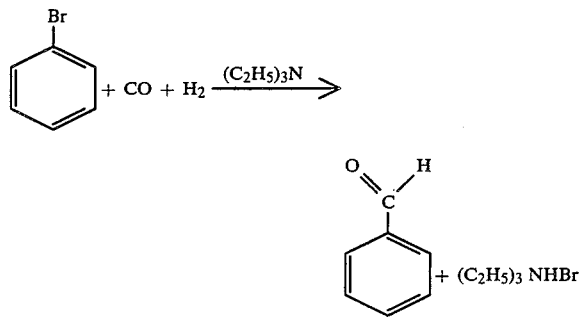

The process of the invention makes it possible to produce aldehydes of the formula

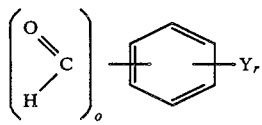

in which Y, r and o have the abovementioned meaning.

The process of the invention can be carried out, for example, as follows:

An autoclave is charged with the iodo-, bromo- and/or chloro-aryl compound, the tertiary amine, the solvent, the noble metal catalyst and the promoter. The reaction mixture is heated with stirring while a carbon monoxide/hydrogen mixture is passed in. The reaction is carried out until gas is absorbed no longer. The reaction mixture is cooled down, the autoclave is let down, and the precipitated salt of the teritary amine is separated off by filtration. The reaction product is separated into its components by distillation. The catalyst remains in the residue together with the phosphane or the phosphite and can be recovered in a manner known per se and be used for further reactions.

The distillation residue can also be used directly in further reactions as a catalyst/promoter mixture.

The process of the invention can be carried out batchwise or as a continuous operation.

In the process of the invention, catalyst consumption is markedly reduced and the space-time yield is significantly increased. It is surprisingly possible in the process of the invention to formylate even chloroaryl compounds. This increased activity of the catalyst is particularly surprising, since it is known that phosphanes used, for example, as selectivity-improving additives in hydroformylation reactions reduce catalyst activity (New Syntheses with Carbon Monoxide, 93 and 94 (1980)).

Aldehydes prepared by the process of the invention can also be used as intermediates for crop protection agents (German Offenlegungsschrift No. 2,757,066, German Offenlegungsschrift No. 2,916,358, U.S. Pat. No. 4,191,768 and U.S. Pat. No. 3,992,446).

EXAMPLES

A 0.3 liter stainless steel autoclave is charged with 0.20 mol of an aryl halide, 0.22 mol of triethylamine or tributylamine, 80 ml of solvent and the amount of $PdCl_2(Pph_3)_2$ catalyst and promoter given in Table 1. The mixture is heated with stirring under carbon monoxide/hydrogen pressure to the specified temperature and the pressure is held within the specified range by injecting more gas at regular intervals until gas is no longer absorbed. The mixture is cooled down, the autoclave is let down, the precipitated amine hydrohalide is separated off by filtration, and the filtrate is distilled and analysed by gas chromatography. The values obtained are summarized in Table 1.

TABLE 1

| No. | Aryl halide | Aldehyde | Catalyst [% by weight] | Promoter to catalyst ratio | Promoter | Temperature °C. | Pressure bar | Yield % | Space-time yield |
|---|---|---|---|---|---|---|---|---|---|
| 1 | Bromobenzene | Benzaldehyde | 0.32 | 100 | PPh$_3$ | 175 | 100 | 88 | 22 |
| 2 | Bromobenzene | Benzaldehyde | 2.26 | 100 | PPh$_3$ | 175 | 100 | 95 | 36 |
| 3 | Trifluoromethoxy-bromobenzene | Trifluoromethoxy-benzaldehyde | 0.47 | 85 | PPh$_3$ | 175 | 100 | 93 | 30 |
| 4 | 3,4-Dimethyl-bromobenzene | 3,4-Dimethyl-benzaldehyde | 1.89 | 100 | PPh$_3$ | 175 | 100 | 82 | 22 |
| 5 | 4-Trifluoromethyl-chlorobenzene | 4-Trifluoromethyl-benzaldehyde | 1.94 | 90 | PPh$_3$ | 175 | 100 | 20 | 5 |
| 6 | Bromobenzene | Benzaldehyde | 0.06 | 1,000 | PPh$_3$ | 175 | 100 | 57 | 20 |
| 7 | Bromobenzene | Benzaldehyde | 0.32 | 100 | (p Cl-Ph$_3$P | 175 | 100 | 40 | 25 |
| 8[1] | Bromobenzene | Benzaldehyde | 15.8 | — | — | 125 | 100 | 94 | 0.7 |

[1] Example 8 is a comparative example (J.Am.Chem.Soc. 96, 7761 (1974))
Catalyst in Examples 1 to 7: $PdCl_2(PPh_3)_3$
Catalyst in Example 8: $PdBr_2(PPh_3)_2$
(where Ph represents phenyl)

What is claimed is:

1. In a process for formylating optionally substituted iodo- bromo- and/or chloro-aryl compound with carbon monoxide and hydrogen at a pressure from 20 to 400 bars and at a temperature in the range of 80° to 250° C. in the presence of a noble metal catalyst and a tertiary organic nitrogen compound, the improvement which comprises carrying out the formylation in the presence of a phosphane and/or phosphite, said phosphane and/or phosphite present in an amount of 10 to 1,000 times the molar amount of catalyst.

2. A process according to claim 1 wherein the process is carried out in the presence of a phosphane.

3. A process according to claim 1 wherein the process is carried out in the presence of a phosphite.

4. A process according to claim 1 wherein the process is carried out in the presence of a phosphane of the formula

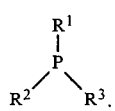

wherein $R^1$, $R^2$ and $R^3$ are identical or different and denote alkyl, cycloalkyl, aryl or aralkyl and the radicals can contain a substituent selected from the group consisting of hydroxyl, alkoxy, carbalkoxy, amino and halogen.

5. A process according to claim 1 wherein the process is carried out in the presence of a phosphite and the phosphite is one of the formula

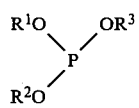

wherein $R^1$, $R^2$ and $R^3$ are identical or different and denote alkyl, cycloalkyl, aryl or aralkyl and the radicals can contain a substituent selected from the group consisting of hydroxyl, alkoxy, carbalkoxy, amino and halogen.

6. A process according to claim 1 wherein the noble metal catalyst is a palladium catalyst.

7. A process according to claim 1 wherein the process is carried out in the presence of a phosphane of the formula

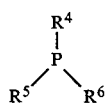 (III)

wherein $R^4$, $R^5$ and $R^6$ are identical or different and denote alkyl having 1 to 20 carbon atoms, cycloalkyl having 1 to 20 carbon atoms, cycloalkyl having 5 to 12 carbon atoms, aralkyl having 7 to 12 carbon atoms or aryl having 6 to 18 carbon atoms, the radicals being optionally substituted by hydroxyl, lower alkoxy, lower carbalkoxy, fluorine, chlorine or amino of the formula

in which $R^7$ and $R^8$ are identical or different and denote lower alkyl or the group

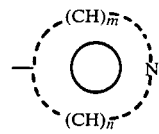

in which the total number of ring atoms is 5 or 6 and m and n represent 0, 1 or 2.

8. A process according to claim 1 wherein the process is carried out in the presence of a phosphite and the phosphite is 1 of the formula

 (IV)

in which $R^4$, $R^5$ and $R^6$ are identical or different and denote alkyl having 1 to 20 carbon atoms, cyclo-alkyl having 5 to 12 carbon atoms, aralkyl radicals having 7 to 12 carbon atoms or aryl radicals having 6 to 18 carbon atoms and the radicals can be optionally substituted by hydroxyl, lower alkoxy, lower carbalkoxy, fluorine, chlorine or amino of the formula

in which $R^7$ and $R^8$ are identical or different and denote lower alkyl or the group

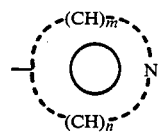

in which the total number of ring atoms is 5 or 6 and m and n represent 0, 1 or 2.

9. A process according to claim 1 wherein the aryl compound is of the formula

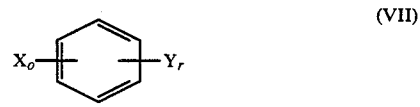 (VII)

in which
X denotes chlorine, bromine or iodine,
o represents one of the numbers 1, 2 or 3, where in the case that o denotes 2 or 3, X can be identical or different,
r represents one of the numbers 1, 2, 3, 4 or 5 and
Y can be identical or different if r represents one of the numbers 2, 3, 4 or 5, and denotes hydrogen, fluorine, alkyl, aryl or one of the groups $-OR$, $-\overset{O}{\underset{\|}{C}}-OR$, $-O-\overset{O}{\underset{\|}{C}}-R$, $-OCF_3$, $-OCCl_3$, $-SR$, -continued

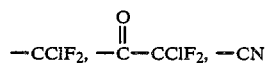

wherein R represents alkyl or aryl, and where in the case that two Ys are adjacent, they can be bonded to form a ring.

10. A process according to claim 1 wherein the aryl compound is an iodo-, bromo- and/or chloro-aryl aromatic of the formula

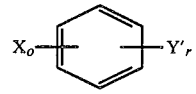 (VIII)

in which,
X denotes chlorine, bromine or iodine,
o represents one of the numbers 1, 2 or 3, wherein the case that o denotes 2 or 3, X can be identical or different,
r represents one of the numbers 1, 2, 3, 4 or 5,
Y, if r represents one of the numbers 2, 3, 4 or 5, can be identical or different and denote hydrogen, chlorine, alkyl having 1 to 20 carbon atoms, phenyl or one of the groups —OR', —OCF$_3$, —OCCl$_3$, —SR', —CClF$_2$ or —CN,
wherein R' represents alkyl having 1 to 20 carbon atoms or phenyl, and wherein if two Y's are adjacent they can be bonded to form a ring.

* * * * *